(12) United States Patent
Frantz et al.

(10) Patent No.: US 10,722,438 B2
(45) Date of Patent: Jul. 28, 2020

(54) HAIR COLORING CONDITIONER FOR RED HAIR

(71) Applicant: Kao USA Inc., Cincinnati, OH (US)

(72) Inventors: Seren Frantz, Cincinnati, OH (US); Amy Jones Davis, Cincinnati, OH (US)

(73) Assignee: Kao USA Inc., Cincinnati, OH (US)

(*) Notice: Subject to any disclaimer, the term of this patent is extended or adjusted under 35 U.S.C. 154(b) by 0 days.

(21) Appl. No.: 15/812,014

(22) Filed: Nov. 14, 2017

(65) Prior Publication Data

US 2019/0142720 A1    May 16, 2019

(51) Int. Cl.
| | | |
|---|---|---|
| A61Q 5/10 | (2006.01) | |
| A61K 8/41 | (2006.01) | |
| A61Q 5/12 | (2006.01) | |
| A61K 8/89 | (2006.01) | |
| A61K 8/49 | (2006.01) | |
| A61K 8/92 | (2006.01) | |
| A61K 8/42 | (2006.01) | |
| A61Q 5/06 | (2006.01) | |

(52) U.S. Cl.
CPC .............. *A61K 8/416* (2013.01); *A61K 8/415* (2013.01); *A61K 8/42* (2013.01); *A61K 8/49* (2013.01); *A61K 8/4926* (2013.01); *A61K 8/4946* (2013.01); *A61K 8/89* (2013.01); *A61K 8/92* (2013.01); *A61Q 5/065* (2013.01); *A61Q 5/10* (2013.01); *A61Q 5/12* (2013.01)

(58) Field of Classification Search
CPC . A61Q 5/10; A61Q 5/065; A61Q 5/12; A61K 8/416; A61K 8/89; A61K 8/92; A61K 8/42
See application file for complete search history.

(56) References Cited

U.S. PATENT DOCUMENTS

| | | | |
|---|---|---|---|
| 4,954,335 A | 9/1990 | Janchipraponvej | |
| 6,365,142 B1 | 4/2002 | Tamura | |
| 6,979,439 B1 | 12/2005 | Sakai et al. | |
| 9,289,630 B2 * | 3/2016 | Lee | A61K 8/342 |
| 2012/0017931 A1 * | 1/2012 | Frohling | A61K 8/416 |
| | | | 132/208 |

FOREIGN PATENT DOCUMENTS

EP    1127566 A2    8/2001

* cited by examiner

*Primary Examiner* — Eisa B Elhilo
(74) *Attorney, Agent, or Firm* — Frost Brown Todd LLC

(57) ABSTRACT

A composition for producing a natural looking red hair color over a wide range of red hair tones, including warm and cool tones, through the daily use of a hair conditioning color treatment.

7 Claims, 1 Drawing Sheet

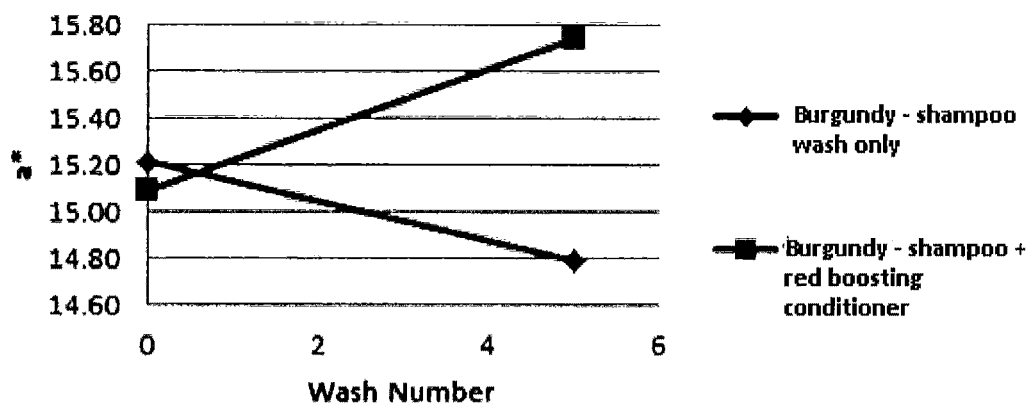

HAIR COLORING CONDITIONER FOR RED HAIR

FIELD OF THE INVENTION

The present invention is directed to a hair coloring conditioner composition for producing a natural looking red hair color over a wide range of red hair tones through the daily use of a hair conditioning coloring treatment.

BACKGROUND

Hair conditioners are produced in a variety of types with an ever-increasing number of claimed benefits. Many of these benefits go beyond traditional hair conditioning, moisturization, or detangling, and include hair reconstruction, pH balancing, and several cross-category benefits such as color deposition and cleansing. Rinse-off type conditioners are among the most common forms. Among those, rinse-off types of conditioners have always been preferred in hair care. Usually, rinse-off type conditioners are in the form of emulsions and comprising fatty alcohols and emulsifiers of different character as the main principal ingredients. In addition, they certainly comprise conditioning ingredients of various types and those of common ingredients in cosmetic preparations. A general overview on the known hair conditioning products and also their usual compositions can be found in the monography of K. Schrader, "Grundlage and Rezepturen der Kosmetika", 2nd Ed. 1989, pp 722-781.

Coloring conditioners have been known for a long time. Those are mainly, as the ones without dyestuff, in an emulsion form and contain those fatty alcohol and emulsifiers as the main ingredients. EP 1 127 566 A2 discloses coloring conditioners based on a cationic polymer and direct dyes.

Current hair conditioners targeted at red hair typically produce an unnatural appearance. As red hair ranges from warm and bright tones such as copper to cool tones such as mahogany/burgundy, it is a challenge to formulate a single product that provides benefits across the entire range of red tones. Through a unique combination of basic dyes used in conjunction with dye-enhancing technology, a hair conditioner has been developed that overcomes these challenges.

BRIEF SUMMARY

The hair coloring conditioners of the present invention produce a natural looking red hair over a wide range of red tones, including both warm and cool tones, through the use of a daily hair conditioning treatment. The conditioner is designed for use on both cool and warm tones of color-treated red hair to enhance natural-looking red color between permanent hair colorings. The hair coloring conditioner may also be used on natural, non-color treated red hair to enhance natural red hues.

In addition, the hair coloring conditioner is optimized to minimize the build-up of conditioning agents that could prevent dye deposition. Since cationic dyes compete for the same spots on the hair shaft as the basic dye, it could be beneficial to use at least a portion of the cationic surfactants as alkyl amine salts to reduce the competition for negatively charged sites on the hair shaft.

BRIEF DESCRIPTION OF FIGURES

The FIGURE displays numerical values of increase in red color over five washes with representative example. This technology produces a cumulative effect of increase in *a (red color).

DETAILED DESCRIPTION

The FIGURE displays numerical values of increase in red color over five washes with representative example. This technology produces a cumulative effect of increase in *a (red color).

This technology produces natural looking red hair over a wide range of red hair tones, including both cool and warm tones, through the daily use of a conditioning treatment. The hair coloring conditioner may also be used on natural, non-color treated red hair to enhance natural red hues.

This technology is optimized by total levels of the dyes and the ratio between the dyes.

This hair coloring conditioner composition is for application to wet (towel-dried) hair and comprises: at least three dyes comprising a basic red dye 51, a basic blue dye; and a dye selected from the group consisting of basic orange, basic yellow, and basic brown; an amidoamine; and a conditioning composition as the carrier.

Some useful basic dyes, used in the coloring conditioners according to the invention may include:
  Basic Blue 6, C.I.-No. 51,175;
  Basic Blue 7, C.I.-No. 42,595;
  Basic Blue 9, C.I.-No. 52,015;
  Basic Blue 26, C.I.-No. 44,045;
  Basic Blue 41, C.I.-No. 11,154;
  Basic Blue 99, C.I.-No. 56,059;
  Basic Blue 124
  Basic Brown 4,
  Basic Brown 16; C.I.-No. 12,250;
  Basic Brown 17, C.I.-No. 12,251;
  Natural Brown 7, C.I.-No. 75,500;
  Basic Green 1, C.I.-No. 42,040;
  Basic Red 2, C.I.-No. 50,240;
  Basic Red 22, C.I.-No. 11,055;
  Basic Red 15
  Basic Orange 31
  Basic Violet 1, C.I.-No. 42,535;
  Basic Violet 3, C.I.-No. 42,555;
  Basic Violet 10, C.I.-No. 45,170;
  Basic Violet 14, C.I.-No. 42,510;
  Basic Yellow 57, C.I.-No. 12,719.
  HC Blue No. 2
  HC Blue No. 4
  HC Blue No. 5
  HC Blue No. 6
  HC Blue No. 7
  HC Blue No. 8
  HC Blue No. 9
  HC Blue No. 10
  HC Blue No. 11
  HC Blue No. 12
  HC Blue No. 13
  HC Brown No. 1
  HC Brown No. 2
  HC Green No. 1
  HC Orange No. 1
  HC Orange No. 2
  HC Orange No. 3
  HC Orange No. 5

HC Red BN
HC Red No. 1
HC Red No. 3
HC Red No. 7
HC Red No. 8
HC Red No. 9
HC Red No. 10
HC Red No. 11
HC Red No. 13
HC Red No. 14
HC Violet BS
HC Violet No. 1
HC Violet No. 2
HC Yellow No. 2
HC Yellow No. 4
HC Yellow No. 5
HC Yellow No. 6
HC Yellow No. 7
HC Yellow No. 8
HC Yellow No. 9
HC Yellow No. 10
HC Yellow No. 11
HC Yellow No. 12
HC Yellow No. 13
HC Yellow No. 14
HC Yellow No. 15

For the current technology, the red dye is a basic dye and is preferably Basic Red Dye 51.

For the current technology, the blue dye is a basic dye and is preferably Basic Blue 99 or Basic Blue 124.

For the current technology, the third dye may be a basic orange dye, for instance, Basic Orange 31.

For the current technology, the third dye may also be a basic yellow dye, for instance Basic Yellow 87

For the current technology, the third dye may also be a basic brown, for instance Basic Brown 17.

The weight ratio of Basic Red Dye 51 to a basic blue dye is from about 8:1 to about 1:1, more preferably about 5:1 to about 2:1 and most preferably 4:1 to 2:1.

The weight ratio of Basic Red Dye 51 to a dye selected from the group consisting of basic orange, basic yellow, and basic brown is from about 1:0.7 to about 1:5. More preferably about 1:1 to about 1:1.25.

Amidoamines may also be used, and in particular behenamidopropyl dimethylamine.

Amidoamines can be derived from the reaction of fatty acids with polyamines that contain at least one tertiary amine group. Some examples include stearamidopropyl dimethylamine (Lexamine® S-13, Inolex Chemical Company, Philadelphia, Pa., USA) which is the reaction product of stearic acid (linear, C-18) with dimethylaminopropylamine. Behenamidopropyl dimethylamine (Lexamine® B-13, Inolex Chemical Company, Philadelphia, Pa., USA) is the reaction product of behenic acid (linear, C-22) with dimethylaminopropylamine. Stearamidoethyl diethylamine (Lexamine® 22, Inolex Chemical Company, Philadelphia, Pa., USA) is the reaction product of stearic acid (linear, C-18) with diethylaminoethylamine Each of these products has been used successfully for many years alone or in combination with other types of conditioning ingredients in hair conditioning compositions. The amidoamines of this invention may have straight/linear or branched carbon chains. The amidoamines of this invention may range from C8 to C24, most commonly C18 to C22. The amidoamines of this invention are typically fatty acid amidoproyl dimethylamines.

Representative patents directed to use of amidoamines in hair formulations include U.S. Pat. No. 4,954,335, which describes the usefulness of amidoamines in the formulation of clear hair conditioners. U.S. Pat. No. 6,365,142 also discloses the use of amidoamines in combination with other ingredients to form a hair conditioner. U.S. Pat. No. 6,979,439 discloses the use of amidoamines in anti-dandruff preparations. Although the prior art discloses the possible use of amidoamines in combination in hair care formulations, there have been no disclosures that suggest a particular advantage of any such combinations. Additionally, applicants are unaware of a particular theory that has been applied to account for or predict any a potential relationship between chemical structure and physical properties that would serve as a basis for one skilled in the art to predict the benefits or outcome of particular combinations of such compounds other than what would be expected in terms of general additive contributions of individual components.

Although the prior art discloses the possible use of amidoamines in combination in hair care formulations, there have been no disclosures that suggest a particular advantage of any such combinations. Examples of amidoamine include AMIDET®. (Behenamidopropyl Dimethylamine); Cocamidopropyl Dimethylamine, and Stearamidopropyl Dimethylamine.

These amine groups become positively charged in aqueous solutions because of their electron-donating (basic) tendencies, yielding a cationic molecules. These cationic molecules deposit onto the hair because of the electrostatic attraction between the positively-charged polymers and the hair itself. The charge density of these molecules can be varied by changing the placement and quantity of the amine groups. A polymer with greater charge density will be more substantive to the hair than one with lesser charge density.

The hair coloring conditioner compositions of the present invention can be formulated using standard conditioner components, together with the required components defined above. The amount of oily materials utilized is generally kept low since one of the benefits of the present invention is that conditioner compositions can be formulated to provide effective results without imparting a great deal of oily materials to the hair. For example, the total amount of conditioning materials in the composition (e.g., fatty alcohols, fatty acids, alkyl quaternary ammonium compounds, and oil agents) is typically less than about 10% of the composition, the compositions can have a viscosity of at least about 5,000 centipoise, Water can be the primary solvent of the compositions of the present invention. For example, such compositions can include at least about 70% water, for example at least about 80% water, or at least about 90% water.

The hair coloring conditioner compositions may contain organic ingredients, for example, ethanol, propanol, isopropanol, cyclohexane, cyclohexanol, hexyleneglycol, ethylene glycol, butylene glycol, propylene glycol, ethylene glycol monoethylether, ethylene glycol monobutyl ether, ethylene glycol monophenyl ether, Concentration of organic solvents in the conditioner composition can be in the range from 0.01% to 10% by weight, preferably 0.1% to 7.5% by weight, and more preferably 0.1% to 5% by weight calculated to the total composition. The organic solvents may at the same time serve to solubilize ingredients which are not readily soluble in the conditioner composition.

The hair coloring conditioners of the present invention can optionally include volatile cyclomethicones, well-known in the hair conditioner art, as well as non-volatile silicones, such as arylated silicones, such as phenyltrimethicone or dimethiconol. In addition, naturals oils, such as olive oil, almond oil, avocado oil, jojoba oil, coconut oil, palm oil, sunflower oil, peach kernel oil, wheat germ oil, night primrose oil, or soya oil, or their mixtures, can also be included. Concentrations of such oily materials are generally below about 2%, preferably below about 1%, such as below about 0.5%, in order to keep the compositions from leaving a significant oily residue on the hair. Other compositions of the present invention can optionally include fatty acid esters, such as isopropyl myristate, isopropyl palmitate, isopropyl stearate and isopropyl isostearate, oleyl oleate, isocetyl stearate, hexyl laurate, dibutyl adipate, dioctyl adipate, myristyl myristate, oleyl erucate, cetyl palmitate, and mixtures thereof. Cationic surfactants, such as cetyl trimethyl ammonium chloride, and behentrimonium chloride, can also be included. If utilized, all of these materials are utilized at low levels. Natural plant extracts can also be included at their art-established hair conditioner levels.

Glyceryl esters, at levels of from about 3.5% to about 10% of the composition, such as esters of coconut fatty acid, palm kernel fatty acid, palm oil fatty acid, lauric acid, myristic acid, caprylic acid, capric acid, and oleic acid, can be included. Polyethylene or polypropylene glycol can be included at from about 0.3% to about 2% of the composition. Glycerin can be included at from about 1% to about 20% of the composition.

Hair coloring conditioner compositions of the present invention can optionally contain non-ionic polymers such as hydroxyethylcellulose, hydroxypropylclellulose, xyloglucan, polyvinylalcohol, polyvinylpyrrolidone or their derivatives.

The hair coloring conditioner compositions may have viscosity values between 1,000 mPa·s to 300,000 mPa·s, preferably 5,000 mPa·s to 100,000 mPa·s and more preferably 10,000 mPa·s to 70,000 mPa·s measured at 25° C. with Brookfield viscosimeter with, for example, Spindle T-C at 10 rpm. The viscosity values are read after 60 seconds from the start of the measurement. In the selection of the viscosity, special attention must be paid to the way of application and packaging to be used.

The pH of the hair coloring conditioners of the present invention varies from 2 to 7, particularly 2.5 to 6 and more particularly 3 to 6.0.

For adjusting the pH of the said hair coloring conditioner compositions, following ingredients can be used: Organic acids such as citric acid, lactic acid, tartaric acid, malic acid, maleic acid, fumaric acid, levulinic acid, butyric acid and hydroxy butyric acids, valeric acid, oxalic acid, succinic acid, mandelic acid, glycolic acid, glucuronic acid, propionic acid, salicylic acid or acetic acid or inorganic acids such as hydrochloric acid, phosphoric acid, sulfuric acid, nitric acid. Concentration of the organic and/or inorganic acids or their mixtures should be adjusted in a way that conditioner composition so obtained has a pH value between 2 to 7. Typically, concentration for acids can be 0.01-5% by weight, preferably 0.01-4% by weight, more preferably 0.05-2.5% by weight calculated to the total composition. The pH of the conditioner composition can also be adjusted to the required pH by using alkaline solution such as sodium hydroxide, potassium hydroxide or their salts with those acids mentioned above in the case that at the selected acid concentration pH of the composition is lower than that of the aimed value.

The hair coloring conditioner composition may contain active ingredients selected from moisturizers, conditioning agents and natural ingredients.

The moisturizing agents are selected from panthenol, polyols, such as glycerol, polyethylene glycols with molecular weight 200 to 20,000. The moisturizing ingredients can be included in the conditioner compositions at a concentration range of 0.01-10% by weight calculated to the total composition.

Fragrances, chelating agents, preservatives, colorants and other conventional cosmetic ingredients can also be included at their usual concentrations for use in hair conditioner compositions.

Nonionic surfactants, such as sorbitan esters, C10-C22 fatty alcohol alkoxylates and alkyl polyglucocides can also be included, at their art-established usage levels.

Hair coloring conditioners compositions of the present invention can also optionally comprise conventionally-utilized UV filters either for stabilization of the product color, such as loss of elasticity or loss of hair color (or both).

The hair coloring conditioner compositions of the present invention can be used in the conventional way that a hair conditioner is used, but stronger color deposition is seen with leaving the conditioner on for longer. Specifically, an effective amount of the hair conditioner is worked into the hair (preferably shampooed hair), and is allowed to remain in the hair for a short period of time (e.g., between about 1 minute and about 5 minutes). The composition generally is rinsed out of the hair with water, thereby providing the hair conditioning benefits of the present invention. By "effective amount of conditioner," as used herein, is meant a portion of hair conditioner of approximately 5 to about 20 milliliters, which is applied to and worked into the wet hair.

Natural plant extracts can be used in the conditioners. Those are preferably the extracts from almond, Aloe Vera, coconut, mango, peach, lemon, wheat, rosemary, apricot, algae, grapefruit, sandalwood, lime, pomegranate, plum, blackberry, blueberry, raspberry, beet, poke weed berry, cherry, rose, hibiscus, bloodroot, daylily, huckleberry, indigo, woad, red cabbage, elder berry, mulberry, purple grape, and dogwood bark and orange. Those extracts used are the ones commercially available and generally include organic solvents such as propylene glycol, butylenes glycol, ethanol, isopropanol. The active matter in those extracts can vary largely, i.e. in the range of 1-30% by weight. Concentration of those as an extract depending on the compatibility with the other ingredients can be in the range of 0.1 to 5%, preferably 0.1 to 2% by weight calculated to the total composition.

EXAMPLES

The following examples illustrate specific aspects of the present technology and are not intended to limit the scope thereof in any respect and should not be so construed.

| | Lot #: | | | | | |
|---|---|---|---|---|---|---|
| | Example 1 | Example 2 | Example 3 | Example 4 | Example 5 | Example 6 |
| % Conditioning Waxes | 4.92 | 4.96 | 4.92 | 4.96 | 4.91 | 4.90 |
| % Silicone Oil | 1.97 | 1.98 | 1.97 | 1.98 | 1.97 | 1.96 |

-continued

| | Lot #: | | | | | |
|---|---|---|---|---|---|---|
| | Example 1 | Example 2 | Example 3 | Example 4 | Example 5 | Example 6 |
| % Amidoamine (Behenamidopropyl Dimethylamine + Stearamidopropyl Dimethylamine) | 1.48 | 1.49 | 1.48 | 1.49 | 1.47 | 1.47 |
| % Quaternary Surfactant (Behentrimonium Chloride) | 0.01 | 0.01 | 0.01 | 0.01 | 0.01 | 0.01 |
| Red 51 Wt % | 0.0121 | 0.0061 | 0.0121 | 0.0061 | 0.0120 | 0.0120 |
| Orange 31 Wt % | 0.0151 | 0.0076 | 0.0151 | 0.0076 | 0.0150 | 0.0150 |
| Yellow 87 Wt % | 0.0095 | 0.0048 | 0.0095 | 0.0048 | 0.0095 | 0.0095 |
| Blue 124 Wt % | 0.0030 | 0.0015 | 0 | 0 | 0.0060 | 0.0060 |
| Blue 77 Wt % | 0 | 0 | 0.0030 | 0.0015 | 0 | 0 |
| Brown 17 Wt % | 0 | 0 | 0 | 0 | 0 | 0.0085 |

What is claimed:

1. A hair coloring composition for enhancement of cool and warm red tones for application to wet hair comprising:
   a) at least three dyes comprising a basic red dye 51, a basic blue dye 124, wherein the weight ratio of basic red dye 51 to basic blue dye is from about 4:1 to 2:1; and a dye selected from the group consisting of basic orange, basic yellow, and basic brown dyes;
   b) an amidoamine selected from the group consisting of behenamidopropyl dimethylamine or stearamidopropyl dimethylamine; and
   c) a conditioning composition as a carrier.

2. The hair coloring composition of claim 1, wherein the weight ratio of basic red dye 51 to a dye selected from the group consisting of basic orange, basic yellow, and basic brown dyes is from about 1:0.5 to about 1:1.

3. The hair coloring composition of claim 2, wherein the third dye is Basic Orange 31.

4. The hair coloring composition of claim 3, wherein the amidoamine is present in an amount from about 0.5-5% by weight.

5. A method of imparting a natural looking red color for both cool and warm red tones, between permanent hair colorings for color-treated red hair by applying to towel-dried hair a composition comprising:
   a) a mixture of at least three dyes comprising a basic red dye 51, a basic blue dye 124, wherein the weight ratio of basic red dye 51 to basic blue dye 124 is from about 8:1 to about 1:1; and a basic orange 31 dye;
   b) an amidoamine comprising behenamidopropyl dimethylamine or stearamidopropyl dimethylamine; and
   c) a conditioning composition as a carrier.

6. The method of claim 5, wherein the weight ratio of basic red dye 51 to a basic orange 31 dye is from about 1:0.7 to about 1:1.25.

7. The method of claim 5, wherein the amidoamine is present in an amount from about 0.55% by weight.

* * * * *